(12) United States Patent
Jurgensen et al.

(10) Patent No.: US 7,524,641 B2
(45) Date of Patent: Apr. 28, 2009

(54) METHOD OF SEPARATING CELLS FROM A SAMPLE

(75) Inventors: Stewart Russell Jurgensen, Raleigh, NC (US); Sheila Ann Lloyd, New Hill, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 221 days.

(21) Appl. No.: 11/684,693

(22) Filed: Mar. 12, 2007

(65) Prior Publication Data

US 2007/0190584 A1    Aug. 16, 2007

Related U.S. Application Data

(63) Continuation of application No. 09/756,590, filed on Jan. 8, 2001, now Pat. No. 7,205,157.

(51) Int. Cl.
*G01N 33/536* (2006.01)
*G01N 33/538* (2006.01)

(52) U.S. Cl. ............... 435/7.24; 422/55; 422/58; 422/59; 422/72; 422/73; 422/82.05; 435/7.21; 435/7.25; 435/288.1; 435/288.7; 436/63; 436/164; 436/175; 436/177; 436/514; 436/518; 436/533; 436/536; 436/538; 436/541; 436/805; 436/810; 436/824; 436/825

(58) Field of Classification Search ............ 422/55, 422/58, 59, 72, 73, 82.05; 435/7.21, 7.24, 435/7.25, 288.1, 288.7; 436/63, 164, 175, 436/177, 514, 518, 533, 536, 538, 541, 805, 436/810, 824, 825
See application file for complete search history.

(56) References Cited

U.S. PATENT DOCUMENTS

| | | | | |
|---|---|---|---|---|
| 4,027,660 A * | 6/1977 | Wardlaw et al. | ............ | 600/584 |
| 4,077,396 A * | 3/1978 | Wardlaw et al. | ............ | 600/309 |
| 4,082,085 A * | 4/1978 | Wardlaw et al. | ............ | 600/309 |
| 4,137,755 A * | 2/1979 | Wardlaw et al. | ........... | 73/61.43 |
| 4,159,896 A * | 7/1979 | Levine et al. | ............... | 436/177 |
| 4,567,754 A * | 2/1986 | Wardlaw et al. | ........... | 73/61.43 |
| 5,393,674 A * | 2/1995 | Levine et al. | ............... | 436/177 |
| 5,635,362 A * | 6/1997 | Levine et al. | .............. | 435/7.24 |

* cited by examiner

*Primary Examiner*—Christopher L Chin
(74) *Attorney, Agent, or Firm*—Mark Lindsey

(57) ABSTRACT

Rare cells are separated from a sample fluid by a positive selection or negative selection antibody by centrifuging in a tube containing a harvesting float. The harvesting float has an axial passage and a density to settle in the sample fluid and expand the layer of the target component. The positive selection antibody is preferably coupled to a particulate carrier, such as a microbead, to attach to the target component. The negative selection antibody forms a complex or conjugate with a contaminating component. In the positive separation, the particulate carrier is recovered in the axial passage of the float.

13 Claims, 4 Drawing Sheets

METHOD OF SEPARATING CELLS FROM A SAMPLE

This application is a continuation of U.S. patent application Ser. No. 09/756,590 filed Jan. 8, 2001, which is hereby incorporated by reference.

FIELD OF THE INVENTION

The present invention is directed to a method of separating a target component and particularly target cells from a sample. More particularly, the invention is directed to a method of separating target cells from a biological sample by positive or negative separation and centrifugation.

BACKGROUND OF THE INVENTION

Numerous methods are known in the art for separating various constituents from biological fluids, and particularly blood samples. For example, the analysis of blood components typically involves the centrifugation of anti-coagulated whole blood to separate the cells from plasma and to separate the various cells into layers according to the density of the cells. After centrifugation, the plasma fraction is removed from the sample. Blood collection is often performed in an evacuated tube and then cell separation is achieved by centrifugation of the collection tube. The tube can contain a separator body that is made of a plastic material with a specific gravity that will enable the separator to settle during the centrifugation step onto the top of the formed component layer in the blood sample. The separator prevents mixing of the formed and unformed component fractions in the centrifuged blood sample. The separator also stabilizes the centrifuged layers for separation and analysis.

Another method of recovering cells from a blood sample uses a hollow insert placed in the centrifuge tube that contains the sample prior to centrifugation. The insert is made of a transparent plastic material and fits within the centrifuge tube. The insert slides within the tube when centrifuged to force the sample into the bore of the insert. The cells to be harvested from the sample collect in the bore of the insert thereby forming layers of constituents that separate according to the specific gravity of the constituents. The bore of the insert has a dimension to cause the layers to elongate in comparison to the thickness of the layer that would otherwise form in the tube without the insert. The resulting layers in the bore can be differentiated and removed from the bore using a hypodermic syringe or other cannula. An example of this process and device are disclosed in U.S. Pat. No. 5,393,674 to Levine et al.

Another method and apparatus for separating constituents from a sample are disclosed in U.S. Pat. No. 5,707,876 to Levine. This device uses one or more boundary makers that are placed in the tube before centrifugation. The markers slide within the tube when centrifuged and identify boundaries of the constituent layers that gravimetrically separate during centrifugation. A cannula is inserted into the tube through an elastomeric cap for injecting a liquid or gas into the tube. The injected material displaces the centrifuged sample and the boundary markers to one end of the tube to express the centrifuged sample from the tube.

Other methods of separating components from a biological sample use paramagnetic microbeads having an antigen coupled thereto. The sample is mixed with the microbeads and incubated to bind the constituent to the microbead. The sample is then subjected to magnetic separation. An example of this type of method is disclosed in U.S. Pat. No. 5,916,818 to Irsch et al.

These prior processes have been generally effective for their intended purpose. However, there is a continuing need in the industry for improved methods for separating cells from a biological sample.

SUMMARY OF THE INVENTION

The present invention is directed to a method for separating cells from a sample, and particularly a biological sample. Accordingly, a primary object of the invention is to provide a method for harvesting a specific constituent from a biological sample.

Another object of the invention is to provide a method for the separation of a specific constituent from a biological fluid in higher concentrations than can be obtained by prior methods.

A further object of the invention is to provide a method for harvesting selected cells from a biological fluid with low levels of contaminating constituents.

Still another object of the invention is to provide a method for harvesting rare cells from a biological fluid where the harvested rare cells are substantially free of mononuclear cells.

Another object of the invention is to provide a method for harvesting cells from a biological sample using a particulate carrier having a coating of an antibody having an affinity for a target cell in the sample.

A further object of the invention is to provide a method for harvesting a target constituent from a biological sample using microbeads coated with an antibody having an affinity for white blood cells.

Another object of the invention is to provide a method of separating a target component from a biological sample by centrifuging the sample in the presence of a float having an axial bore after combining the sample with a binding agent having an affinity for at least one component of the sample.

Still another object of the invention is to provide a method for harvesting a target component from a biological sample by centrifuging the sample in the presence of a particulate carrier having a positive or negative selectivity for the target component.

Another object of the invention is to provide a method of harvesting cells from a biological sample by mixing the sample with an amount of carrier particles containing an antibody having an affinity for white blood cells and where the particles have a density greater than the density of white blood cells for removing white blood cells from the sample.

A further object of the invention is to provide a method of harvesting target cells from a biological sample by mixing the sample with an amount of carrier beads containing an antibody having an affinity for the target cells and the beads having a density less than the density of white blood cells for removing the target cells from the sample.

Still another object of the invention is to provide a method for separating target cells from a sample and detecting the target cells in a tube, where the target cells are separated by mixing the sample with carrier beads having an affinity for either the target cells or contaminating cells.

The objects and advantages of the invention are basically attained by providing a method of harvesting components from a sample material. The method comprises the steps of providing a sample material in a sampling container, the sampling container having a focusing device with a passage for receiving and elongating layers of sample components to be harvested from the sample, providing at least one antibody in the sampling receptacle, and mixing the antibody with the sample, wherein the antibody has an affinity for binding with at least one substance in the sample, and centrifuging the container and sample at sufficient G forces to separate components from the sample and to force a target component from the sample into the through passage.

The objects of the invention are further attained by providing a method of harvesting a target component from a whole blood sample. The method comprises the steps of providing a whole blood sample in a sampling tube, the sampling tube containing a float dimensioned to fit within the sampling tube and having a through passage for receiving and elongating layers of blood constituents to be harvested from the sample, mixing the sample with at least one particulate carrier containing an antibody having a binding affinity for a specific sample constituent, centrifuging the tube and sample at sufficient G forces to move the float toward one end of the tube and to force a target component from the sample into the through passage, and removing the target component from the through passage.

The objects of the invention are also attained by providing a method of harvesting a target component from a whole blood sample. The method comprises the steps of providing a whole blood sample in a sampling tube, the sampling tube containing a float dimensioned to fit within the sampling tube and having a through passage for receiving and elongating layers of blood constituents to be harvested from the sample, mixing the sample with an amount of first carrier beads having a coating of a first antibody that has a binding affinity for a target constituent in the sample and an amount of second carrier beads having a coating of the second antibody that has a binding affinity for white blood cells, centrifuging the tube and sample at sufficient G forces to move the float toward one end of the tube and to force the first carrier beads and target constituent into the through passage, and removing the first carrier beads and target constituent from the through passage.

These objects, advantages and other salient features of the invention will become apparent from the in view of the annexed drawings and the following detailed description of the invention.

BRIEF DESCRIPTION OF THE DRAWINGS

The following is a brief description of the drawings in which.

DETAILED DESCRIPTION OF THE PREFERRED EMBODIMENTS

Figure 1:
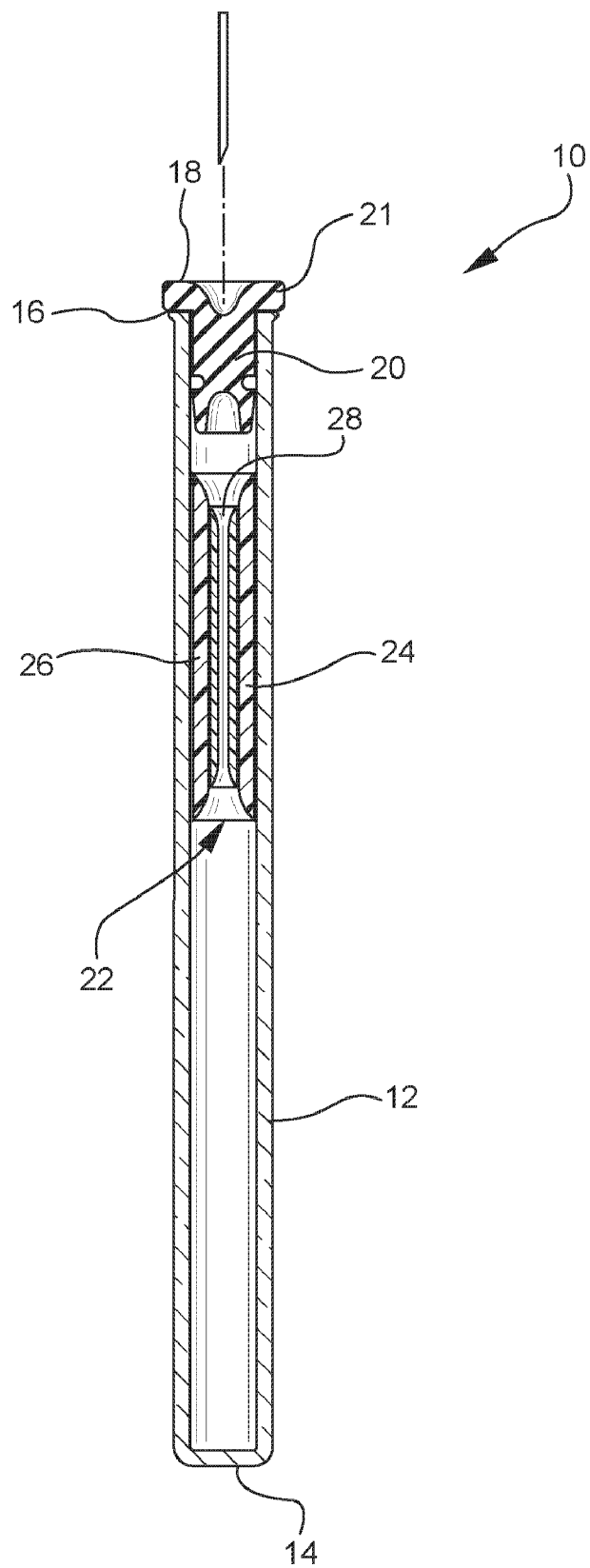
FIG. 1 is a cross-sectional side view of the centrifuge tube in one embodiment of the invention showing a float member positioned in the tube.

The present invention is directed to methods for harvesting a target component and particularly target cells from a biological sample. More particularly, the invention is directed to methods for harvesting rare cells from a biological sample with fewer contaminating cells present in the harvested rare cells.

In a preferred embodiment, the method of harvesting a target component utilizes at least one binding agent capable of binding with a component of the sample to assist in isolating or enhancing the target component during centrifugal separation. The binding agent can be an antibody selected to have an affinity for either the target component or one or more contaminating components. In preferred embodiments of the invention, the affinity binding agent, such as an antibody, is provided as a coating on a particulate carrier having a particle size and density that is compatible with the component being harvested to enhance separation and recovery of the target component from the sample. In the embodiments of the invention discussed below in greater detail, the particulate carrier can have a density lighter or heavier than the density of the contaminating constituent of the sample.

In further embodiments, the method is directed to harvesting rare cells and particularly tumor cells from biological samples and particularly anticoagulated whole blood samples. The method can be used to recover a variety of other cell types, such as stem cells and fetal cells, from blood samples.

The method of the invention in one embodiment subjects the biological sample to centrifugal separation, where the sample is mixed with a particulate carrier having an antibody or other affinity binding agents bound to the surface of the particulate carrier. The centrifugation step preferably uses a centrifuge harvesting device. The antibody is preferably provided as a coating on the surface of the particulate carrier. The particulate carrier in preferred embodiments is an amount of microbeads made of a suitable nonreactive plastic resin. Examples of suitable plastic resins include polystyrene, polydivinylbenzene and polyvinylchloride.

The microbeads for use in the method of the invention can be produced by various methods as known in the art. In embodiments of the invention, the microbeads have a particle size ranging from about 0.05 microns to about 7 microns, and typically about 4 microns to about 5 microns.

The particulate carrier, such as the plastic microbeads, have a density that complements the various components of the sample to enable enrichment of the target component and particularly to enable enrichment of rare cells. In one embodiment, the particulate carrier includes an antibody having a binding affinity for the target component, such as tumor cells. In further embodiments, other affinity binding agents can be used. It was generally believed that after centrifugation, tumor cells are concentrated at the interface of the platelet/plasma region and above the denser majority white cells. The tumor cells harvested generally have a high concentration of contaminating mononuclear cells. It has now been found that tumor cells are not always concentrated at the interface between the cell layers and are difficult to recover without significant contamination from other interfering cells. In one embodiment of the invention, the particulate carrier has a density that is lower than the density of white blood cells so that the particulate carrier and the tumor cells that are bound to or captured on the carrier are concentrated above the layer of white blood cells.

In a first embodiment of the invention, the method of harvesting and enriching a target component is a positive selection process comprising the steps of contacting the sample fluid with a binding agent that is able to bind with the target component, and centrifuging the sample with a device capable of expanding constituent layers and enriching the target component. The target component can then be harvested and further processed to identify and culture the component by known methods. Examples of suitable identifying processes include flow cytometry and molecular nucleic acid amplification.

Figure 2:
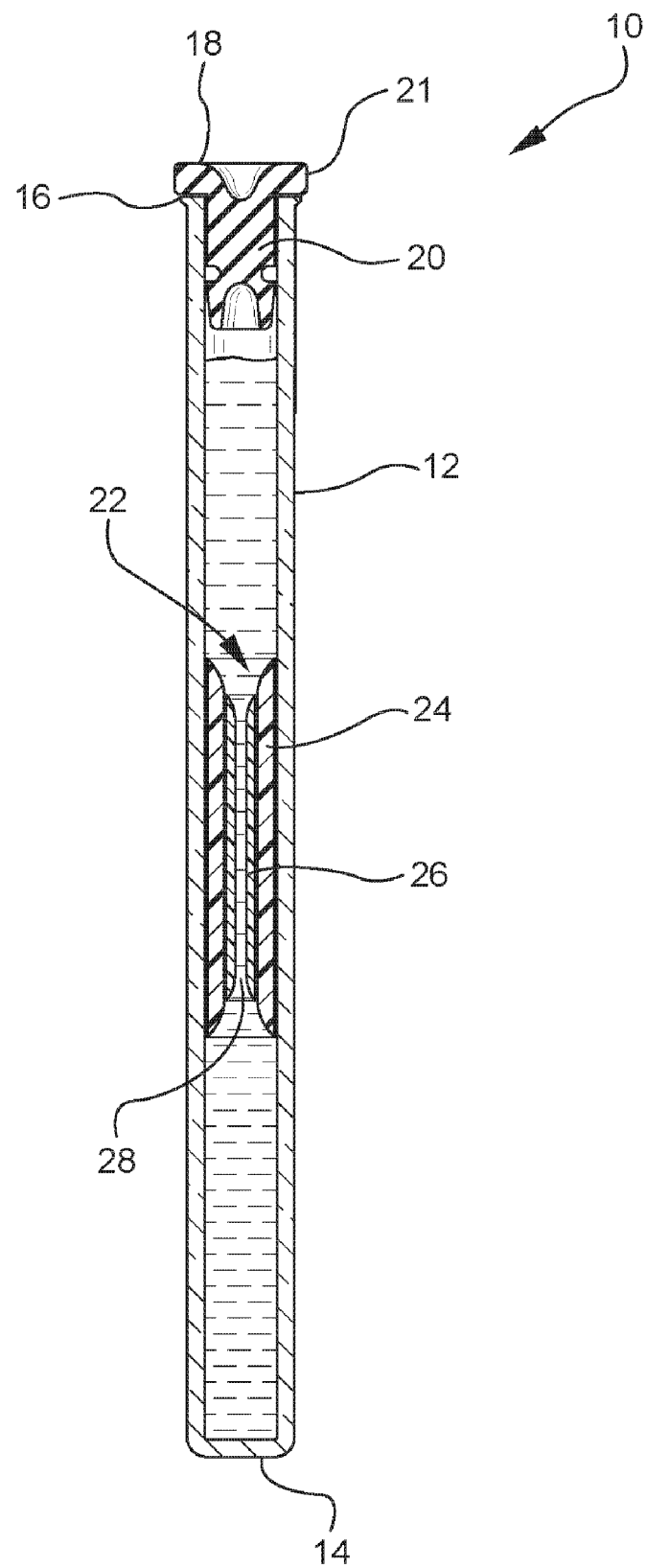
FIG. 2 is a cross-sectional view of the tube of FIG. 1 after centrifugation.

The centrifugation in one embodiment is carried out using a centrifuge device 10 as shown in FIGS. 1 and 2. Device 10 in the embodiment illustrated, includes a container, such as tube 12, that is preferably made of glass or other transparent material, such as plastic. Tube 12 has a closed bottom end 14 and an open top end 16. A stopper 18 is fitted in open top end 16 to close tube 12. Preferably, stopper 18 is made of a suitable elastomeric or rubber-like material that can be pierced by a cannula, needle or other piercing device. Stopper 18 has a substantially cylindrical body portion 20 having an outer dimension to form a snug friction fit in top end 16 of tube 12. A shoulder 21 extends radially outward from an upper end of stopper 18 to engage top end 16 of tube 12.

Tube 12 has a length and diameter suitable for centrifuging a sample fluid. In one embodiment, tube 12 has a length of about 75 mm, an internal diameter of about 40 mm and a capacity of about 0.9 ml.

A float 22 is disposed in tube 12 as shown in FIG. 1. Float 22 is dimensioned to fit snugly in tube 12 and slide along the length of tube 12 during centrifuging of the sample. Float 22, in the embodiment illustrated, includes an outer sleeve 24 having a cylindrical shape complementing the inner surface of tube 12. Outer sleeve 24 is preferably made from a pliable material, such as a vinyl resin, that is able to deform slightly during centrifugation. Outer sleeve 24 can expand and contract in response to the centrifugal force so that float 22 is able to slide within tube 12. The pliable material returns to its original shape and dimensions at static conditions so that outer sleeve 24 snugly contacts the inner surface of tube 12 and is able to slide within tube 12 under centrifugal force. A silicone lubricant can be applied to the inner surface of tube 12 to assist in the sliding movement of the float 22.

Float 22 includes an inner sleeve 26 having an axial passage or bore 28 forming a through passage. Inner sleeve 26 is coupled to outer sleeve 24 by a bonding agent or other suitable method. Inner sleeve 26 is made of a rigid material that is dimensionally stable during centrifugation so substantially no distortion occurs during centrifugation. Axial bore 28 has a length and diameter suitable for expanding a fraction of the sample material during centrifugation. In one embodiment of the invention, axial bore 28 has an inner diameter of about 1.265 mm and a length of about 4.0 mm. Inner sleeve 26 is preferably made from a plastic such as polystyrene that does not interfere with the components of the sample. Float 22 is intended to be exemplary of a suitable centrifuge device capable of separating and expanding a cell fraction. It will be understood that there are other devices that can be used during centrifugation to separate rare cell fractions. Suitable devices typically include a passage or a constricted area for elongating constituent layers during centrifugation to enable separation of the constituent layers.

Float 22 is dimensioned to fit in tube 12 and slide within the tube 12 while centrifuging to settle between selected density layers of the sample fluid and force the target component into the axial bore 28 of float 22. Axial bore 28 of float 22 has an internal volume suitable to collect a substantial portion of the target component. The internal volume and diameter of the float effectively expand the layer of the target component. An example of this type of cell harvesting device is disclosed in U.S. Pat. No. 5,393,674 to Levine et al., which is hereby incorporated by reference in its entirety.

Float 22 is selected to have a density to complement the target component and the sample so that the target component collects in the axial bore 28 by enabling float 22 to settle at a predetermined point in the sample. In one embodiment of the invention, float 22 has a density to settle between the resulting plasma layer and the layer of red blood cells after centrifugation. In this embodiment, the rare cells that normally collect at the interface between the plasma and red blood cell layers collect in the axial bore 28 where they can be recovered.

The sample is centrifuged at a rate sufficient to separate the various constituents into layers. The centrifuge can be at a speed to produce a centrifugal force of about 400 G to about 800 G depending on the sample fluid. In embodiments, the centrifuge can produce a force of 1,000 G or more.

The method of the invention can be a positive selection or a negative selection for harvesting components, and particularly rare cells. In the positive selection method, a sample fluid is mixed with at least one antibody having an affinity for the target component. A negative selection mixes the sample with an antibody having an affinity for the contaminating cells, such as leukocytes and/or red blood cells. Suitable negative selection antibody reagents in the form of specialized conjugates and complexes are available from StemCell Technologies Inc. and Miltenyi Botcher GmbH. Underivatized antibodies are available from other sources such as Pharmagen, Inc. The resulting mixture is then centrifuged using the harvesting float device to harvest the enriched target component. Prior to centrifuging, the sample can be combined with a density gradient media as known in the art to enhance the separation of the target component.

The positive selection harvesting method in one embodiment of the invention utilizes a particulate carrier having a coating of antibody with an affinity toward the target component. In preferred embodiments, the particulate carrier is an amount of plastic microbeads with a coating of an antibody with a binding affinity for the rare cells to be harvested, and particularly tumor cells.

The density of the microbeads and the density of the float are coordinated to collect the microbeads in the axial bore of the float. The positive selection harvesting uses microbeads having a particle size of about 0.05 microns to about 7 microns, and typically about 4 to 5 microns, and a density less than white blood cells. The microbeads can have a density in the range of about 1.00 to about 1.05, and preferably about 1.02 to about 1.03. The microbeads and the captured rare cells have a density so that they are focused in the float when the sample and float are centrifuged. The float has an appropriate density so that the float settles in the sample after centrifuging where the rare cells normally settle. In this embodiment, the microbeads are sufficiently light to float above the centrifuged layers of white and red blood cells. The float preferably has a density to float above the white and red blood cell layers to harvest the microbeads.

The microbeads are made of a suitable material that is non-reactive with the target component and particularly non-reactive with the rare cells. Suitable materials include polyacrylamides, polyurethanes, polysulfones, fluorinated or chlorinated resins, such as polyvinylchloride, polyethylene, polypropylene, polycarbonates and polyesters. The particle is typically about 4 to 5 microns, although the particle size can vary depending on the target component and internal diameter of the float. A number of commercially available microbeads have an antigen bonded to the surface of the microbeads. The antibody can be bonded directly to the surface of the microbead or through an intermediate coupling agent. Suitable antibody coated microbeads are commercially available from Miltenyi Biotec GmbH. An example of a suitable microbead is available from Miltenyi Biotec under the tradename MACS CD 27.

The antibody in the positive selection method has a binding affinity for the rare cells and is selected according to the target rare cells to be harvested from the sample. Examples of rare cells to be harvested include tumor cells, fetal cells and the like. Examples of tumor cells that can be bound to the particulate carrier can be of epithelial origin and can be localized or non-localized. The tumor cells can be of the bladder, brain, breast, colon, kidney, liver, lung, ovary, pancreas, prostate, rectum and stomach. Tumor cells can also be in the form of sarcoma, such as fibrosarcoma or rhabdosarcoma, hematopoietic tumor of the lymphoid or myeloid lineage, melanoma, teratocarcinoma, neuroblastoma, or glioma.

The microbeads preferably have a surface area sufficient to contain an amount of the selected antibody to bind an effective amount of the rare cells being targeted. The amount of the microbeads combined with the sample can vary with the affinity of the antibody, concentration of the rare cells in the sample, the nature of the sample, and the volume of the sample.

The method of the invention is suitable for use in harvesting rare cells from various bodily fluids, and particularly anticoagulated blood. Other fluids that can be analyzed for rare cell content include urine, saliva, lymph fluid, spinal fluid, semen, amniotic fluid, cavity fluids and tissue extracts.

The method is carried out using the centrifuge tube 12 and float 28. In preferred embodiments, tube 12 is evacuated or filled with an inert gas at a subatmospheric internal pressure. The sample to be tested is transferred from a primary collecting tube by a transferring device having a double piercing needle or cannula. The needle extends from the transferring device to the tube by piercing the stopper in tube 12. The low pressure in tube 12 draws the fluid sample into tube 12. A thixotropic gel can be provided in tube 12 as known in the art to preserve band formation in the sample when centrifuged. Various other separation agents, dyes and the like can be added to tube 12 to promote separation and identification of components. The microbeads containing the antibody are provided in the tube 12 and are mixed with the fluid sample by gentle shaking or stirring. The sample is then incubated to bind the target component to the microbeads.

The tube, float and sample are centrifuged at a sufficient speed and for a length of time necessary to separate the constituents of the sample into layers and force the microbeads and the trapped target component into the axial bore of the float. The sample can be centrifuged at a speed to provide sufficient centrifugation force to cause separation of the layers. The tube is slowly stopped and removed from the centrifuge. A needle or cannula then pierces the stopper and is inserted into the axial bore to remove the sample containing the microbeads. The harvested sample is further processed and analyzed by various processes as known in the art. In one embodiment, the harvested cells are analyzed using a flow cytometer. The rare cells or other target components can be washed and separated from the microbeads and the binding antibody by known methods. The resulting harvested rare cells are significantly enriched compared to many prior processes and have a substantially lower contaminant level of red and white blood cells.

In a second embodiment of the invention, the method is a negative selection method for the enrichment of rare cells. The rare cells are enriched using a binding agent that is able to bind with the contaminating non-rare cells, such as red blood cells or white blood cells.

In preferred embodiments, the binding agent is able to bind to one or more white blood cell and/or red blood cell or that bind to surface antigens on the cells. The binding agents can be antibodies that are able to agglutinate the white blood cells or bind the white blood cells to red blood cells. The resulting larger and denser particles can be separated from the non-rare cells during centrifugation. Suitable antibodies that are able to bind with and capture the non-rare cells include antihuman antibodies. Examples of suitable antibodies that can be used to bind with white blood cells (leukocytes) include the leukocyte CD antibodies such as CD2, CD3, CD4, CD5, CD7, CD8, CD11a, CD11b, CD11c, CD14, CD15, CD16, CD19, CD20, CD28, CD36, CD42a, CD43, CD44, CD45, CD45R, CD45RA, CD45RB, CD45RO, CD57 and CD61. Other binding agents that can be used include a mixture of antihuman CD45, antihuman CD19, antihuman CD14 and antihuman CD3.

Preferably, the antibodies are bound to the surface of the microbeads as in the previous embodiments. The microbeads in the negative selection process have a particle size suitable for the sample and the target component. Generally, the particle size ranges from about 0.05 microns to about 7 microns, and preferably about 4 microns to about 5 microns. In this embodiment, the beads preferably have a density greater than the density of white blood cells, and more preferably of about 1.07 to about 1.09 g/ml, and typically in the range of about 1.08 to about 1.09 g/ml. In this manner, the microbeads sink during centrifugation and the rare cells settle above the red and white blood cell layers. The float has density to float on the non-rare cells layers so that the rare cells settle in the axial bore of the float where they can be removed.

The method of the negative selection harvesting is similar to the positive selection discussed above. The sample fluid is provided in the tube and mixed with the microbeads containing the non-rare cell antibodies. After incubating, the tube containing the mixture is incubated and centrifuged for sufficient time to cause the layers to separate and the rare cells to collect in the axial bore of the float where the rare cells can be recovered.

In further embodiments of the invention, the method employs two microbeads having different affinity binding agents for capturing two different components. In one embodiment, an amount of first microbeads having an affinity binding agent with an affinity for rare cells, such as tumor cells, are mixed with the sample. The first microbeads have a density to separate from the white and red blood cells. The first microbeads have a particle size, density and affinity binding agent substantially the same as the microbeads of the positive selection of the previous embodiment. An amount of second microbeads having an affinity binding agent with an affinity for white blood cells is also mixed with the sample. The second microbeads have a density to separate the white blood cells, red blood cells, or a combination thereof from the rare cells. The resulting mixture is centrifuged with the float so that the first microbeads with the captured rare cells settle in the axial passage where they can be recovered. The second microbeads have a particle size, density and affinity binding agent substantially the same as the negative selection method of the previous embodiment. In this manner, the second microbeads separate from the first microbeads during centrifugation to separate the contaminating cells, such as the red and/or white blood cells from the target cells and the first microbeads. The first microbeads have a particle size and density to be collected in the axial passage of the float for recovering the target cells.

Figure 3:
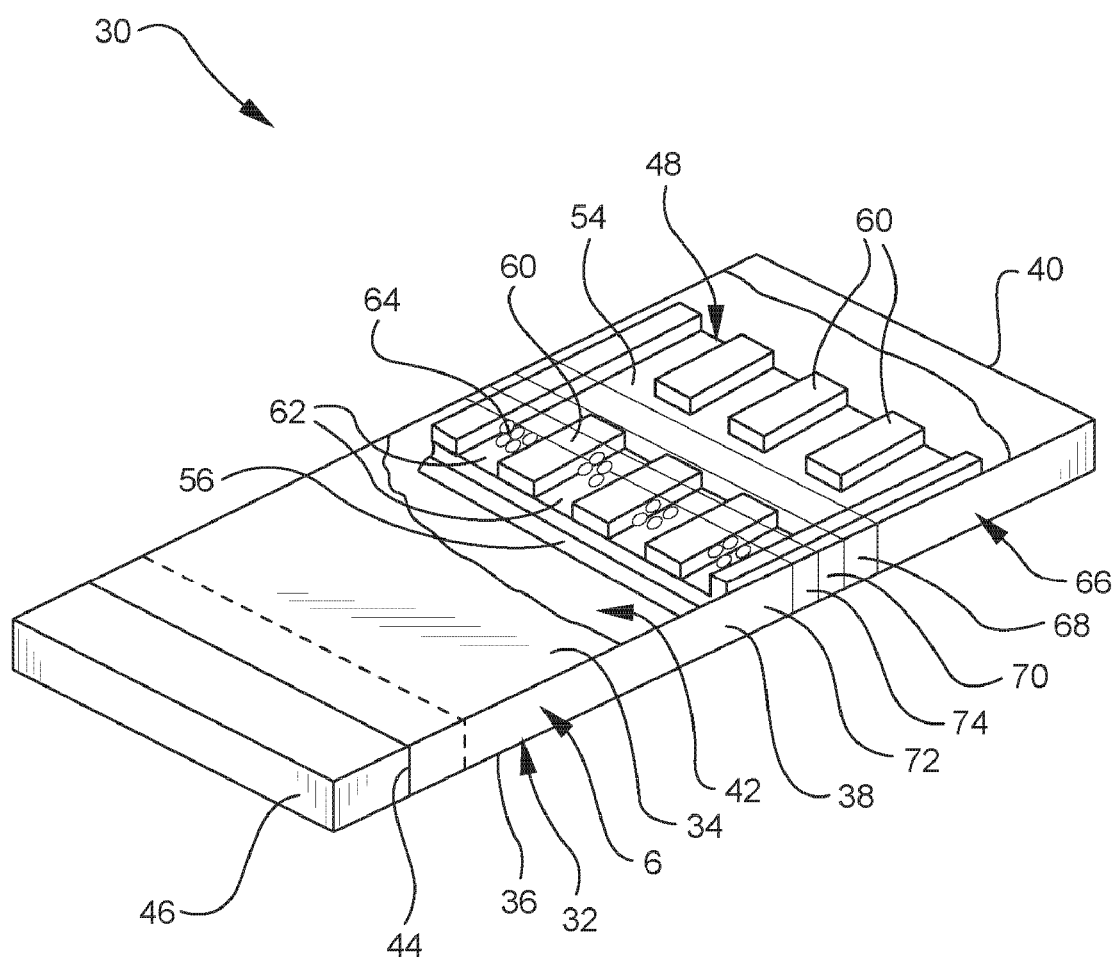
FIG. 3 is a perspective view of a centrifuge separation device in another embodiment of the invention.

Referring to FIG. 3, another embodiment of the centrifuge device 30 is shown. Device 30 is particularly suitable for various cell manipulations after separation from a sample. For example, rare cells can be separated from a sample and subjected to various detection and assay processes with device 30. In this embodiment, device 30 includes a hollow container 32 having a substantially rectangular shape. Container 32 includes a front wall 34, and an opposite rear wall 36 having a longitudinal length and a width. Opposite side walls 38 and a bottom wall 40 extend between front wall 34 and rear wall 36 to form an open cavity 42. Container 32 includes an open end 44 to receive a stopper 46 for closing cavity 42. Preferably, container 32 is made of a transparent material such as glass or plastic.

Container 32 is dimensioned to receive a volume of a biological sample suitable for analysis of a target component. Container 32 generally has a volume of about 8 ml to about 10 ml, and preferably about 9 ml. In the illustrated embodiment, side walls 38 of container 32 have a dimension to define a thickness of cavity 42 that is sufficiently thin to visualize, detect and analyze a target component through front wall 34. Examples of suitable detection and analysis methods include microscopy to visualize cells in the sample. Container 32 is typically about 7 cm to about 8 cm in length, and about 3 cm to about 4 cm in width. Side walls 38 are dimensioned so that cavity 42 has a thickness of about 3 mm to about 6 mm, and preferably about 4 mm.

Figure 4:
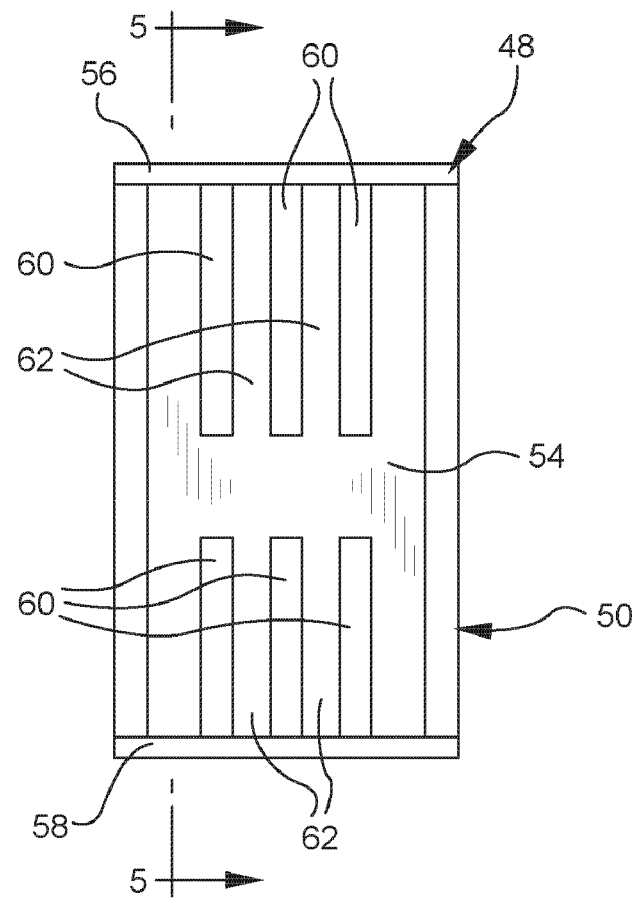
FIG. 4 is a top view of the float of the embodiment of FIG. 3.
Figure 5:
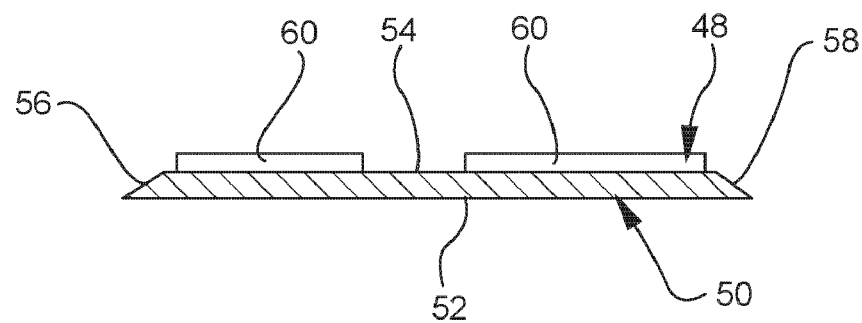
FIG. 5 is a side view in cross-section of the float taken along line 5-5 of FIG. 4.

Container 32 includes a movable float 48 that is able to slide within container 32 in the longitudinal dimension in a manner similar to the previous embodiment. Float 48 is dimensioned to fit within cavity 42 of container 32 and has an outer dimension corresponding to the inner dimension of container 32. As shown in FIGS. 3-5, float 48 has a base 50 with a substantially flat bottom surface 54. Base 50 includes an inclined leading end 56 and an inclined trailing end 58. A plurality of ribs 60 are coupled to top surface 54 of base 50.

As shown in FIG. 5, ribs 60 extend in a longitudinal direction with respect to the longitudinal dimension of base 50. Ribs 60 are aligned in pairs to form channels 62 extending the length of base 50 between adjacent ribs. Ribs 60 have a height to fit closely against the inner surface of container 32. Channels 62 are dimensioned to separate and elongate the layers during centrifugation.

In this embodiment, a biological sample, such as a blood sample, is placed in container 32. An amount of microbeads 64 having an affinity binding agent for a target component is mixed with the sample. Container 32 is then centrifuged as in the previous embodiment to collect the microbeads 64 with the captured target component in longitudinal channels 62 of float 48. Microbeads 52 and the captured target component can then be analyzed by visualizing the target component within container 32 by microscopy methods as known in the art.

In the embodiments shown in FIG. 5, the blood sample after centrifuging separates into a layer of red blood cells 66, a granulocyte cell fraction layer 68, a mononuclear cell fraction 70, a plasma fraction 72 and a platelet/plasma interface 74. In a positive selection process, microbeads 64 have an affinity for the target compound and collect in channels 62. Alternatively, microbeads 64 can have an affinity for white and/or red blood cells in a negative selection process. Channels 62 are formed between ribs 60 and are enclosed by top wall 34 of container 32. Inclined leading edge 56 and inclined trailing edge 58 divert the sample through channels 62 as float 48 slides through container 32. Microbeads 64 are retained in a thin layer in channels 62 close to top wall 34 of container 32 so that the microbeads 64 can be visualized through top wall 34 by microscopy or other analytical methods as known in the art. Preferably, front wall 34 of container 32 is substantially flat to prevent the optical distortion normally associated with cylindrical containers.

EXAMPLE

This example compares the harvested tumor cells from a sample with and without a negative selection. The harvester separations were compared for 6.0 mls of freshly collected whole blood that were spiked with 0, 50 and 500 cultured prostate tumor PC-3 cells. An antibody cocktail obtained from StemCell Technologies, Inc. under the tradename RosetteSep was mixed with each of the blood samples and incubated for 20 minutes at room temperature. A control blood sample was prepared without the antibody treatment. The antibody cocktail provided a negative selection to remove the unwanted white blood cells.

The blood samples were layered on top of a density media in a 16×100 PET Vacutainer tube obtained from Becton Dickinson containing a harvester float and 2 mls of POLYMORPHPREP™ density media. The samples were centrifuged in a swinging bucket centrifuge for 30 minutes at 20□C at a rate of about 650 g. The control sample showed the presence of white blood cells with the tumor cells in the harvester float. The antibody treatment demonstrated tumor cells collected in the harvester float with a greatly reduced white cell population. The tumor cells were removed from the harvester float. Flow cytometry demonstrated recovery of about 90% of the tumor cells.

While various embodiments have been chosen to illustrate the invention, it will be appreciated by those skilled in the art that various modifications and additions can be made without departing from the scope of the invention as defined in the appended claims.

What is claimed is:

1. A method of separating at least one target component from a biological sample, said method comprising
   a. placing said biological sample into a separation container, said separation container comprising
      a focusing device, having an axial bore passage and being capable of vertical movement within said separation container upon centrifugation and a specific density
      a set of selection microbeads having at least one target affinity binding agent bound to their surfaces, said at least one target affinity binding agent having a binding affinity for said at least one target component within said biological sample and
      a negative selection binding agent having a binding affinity for a component other than said target component within said biological sample, such that a complex or conjugate is formed between said negative selection binding agent and said component other than said target component within said biological sample on contact with said biological sample, wherein the specific density of said focusing device is substantially equal to the density of said set of selection microbeads and the specific density of said complex or conjugate formed between said negative selection binding agent and said component other than said target component within said biological sample is different to that of said focusing device and said set of selection microbeads
   b. centrifuging said separation container containing said biological sample to densitometrically separate components of said sample into layers such that separation of said set of selection microbeads and said complex or conjugate formed between said negative selection binding agent and said component other than said target component within said biological sample is induced, wherein an elongated target layer comprising said set of selection microbeads bound to said at least one target component is located within said axial bore passage of said focusing device and wherein said complex or conjugate formed between said negative selection binding agent and said component other than said target component within said biological sample is absent from said axial bore passage of said focusing device after centrifugation; and c. aspirating said elongated target layer to remove said at least one target component from said separation container.

2. The method of claim 1, further comprising mixing said biological sample with said set of selection microbeads and said negative selection binding agent prior to centrifugation.

3. The method of claim 2, wherein said separation container is a cylindrical, closed-end tube with an inner surface, and said focusing device having an outer surface that complements said inner surface of said tube.

4. The method of claim 3, wherein said biological sample is blood.

5. The method of claim 4, wherein said focusing device comprises a single bore axial passage.

6. The method of claim 5, wherein said selection microbeads have a density of between about 1.00 g/cc and about 1.06 g/cc.

7. The method of claim 6, wherein said set of selection microbeads and said negative selection binding agent each comprise at least one antibody.

8. The method of claim 7, wherein said negative selection binding agent binds to the surface of normal white blood cells.

9. The method of claim 7, wherein said negative selection binding agent agglutinates white blood cells.

10. The method of claim 7, wherein said negative selection binding binds white blood cells to red blood cells.

11. The method of claim 7, wherein said negative selection binding agent comprises at least one leukocyte CD antibody.

12. The method of claim 7, wherein said antibody of said set of selection microbeads binds to the surface of cells other than said normal white blood cells.

13. The method of claim 12, wherein said cells other than normal white blood cells are selected from the group consisting of cancer cells and fetal cells.

* * * * *